(12) United States Patent
Renard et al.

(10) Patent No.: US 7,968,735 B2
(45) Date of Patent: Jun. 28, 2011

(54) LIGHT-EMITTING BIOMARKER

(75) Inventors: Pierre-Yves Renard, Paris (FR); Anthony Romieu, Rouen (FR); Marc Massonneau, Tillieres sur Avre (FR)

(73) Assignees: Quidd, Mont-Saint-Aignan (FR); Universite de Rouen, Mont-Saint-Aignan (FR)

( * ) Notice: Subject to any disclaimer, the term of this patent is extended or adjusted under 35 U.S.C. 154(b) by 661 days.

(21) Appl. No.: 11/920,982

(22) PCT Filed: May 24, 2006

(86) PCT No.: PCT/FR2006/050482
§ 371 (c)(1),
(2), (4) Date: Feb. 15, 2008

(87) PCT Pub. No.: WO2006/129036
PCT Pub. Date: Dec. 7, 2006

(65) Prior Publication Data
US 2009/0041669 A1 Feb. 12, 2009

(30) Foreign Application Priority Data
May 27, 2005 (FR) ..................... 05 51396

(51) Int. Cl.
*C07F 7/02* (2006.01)
*G01N 33/543* (2006.01)
*C07G 3/00* (2006.01)
*C07D 405/00* (2006.01)

(52) U.S. Cl. ........ 549/215; 549/219; 549/220; 549/221; 549/232; 436/518; 536/4.1; 548/526

(58) Field of Classification Search .................. 549/215, 549/219, 220, 221, 232, 2; 436/518; 536/4.1; 530/807; 548/526
See application file for complete search history.

(56) References Cited

U.S. PATENT DOCUMENTS
5,330,900 A 7/1994 Bronstein et al.
2004/0077018 A1 4/2004 Giri FOREIGN PATENT DOCUMENTS
| EP | 0 401 001 A2 | 12/1990 |
| EP | 1 342 724 A1 | 9/2003 |
| JP | A 04-051236 | 2/1992 |
| JP | A 04-172338 | 6/1992 |
| JP | A 2003-207366 | 7/2003 |
| JP | A 2004-262817 | 9/2004 |
| WO | WO 90/07511 A1 | 7/1990 |
| WO | WO 94/10258 A1 | 5/1994 |
| WO | WO 96/16137 A1 | 5/1996 |
| WO | WO 96/24849 A1 | 8/1996 |
| WO | WO 00/44719 A2 | 8/2000 |

OTHER PUBLICATIONS

Funovics et al., "Protease sensors for bioimaging", *Anal. Bioanal. Chem.*, vol. 377, pp. 956-963 (2003).
Laxman et al., "Noninvasive real-time imaging of apoptosis", *Proc. Natl. Acad. Sci. USA*, vol. 99, No. 26, pp. 16551-16555, Dec. 24, 2002.
Matsumoto et al., "Chemiluminescent decomposition of a dioxetane bearing a 3-(1-cyanoethenyl)phenyl moiety induced by Michael addition of an anion of malonate", *Tetrahedron Letters*, vol. 45, pp. 3779-3782 (2004).
Matsumoto et al., "Synthesis of bicyclic dioxetanes bearing a 3-hydroxy-r-isoxazolylphenyl moiety: new CIEEL-active dioxetanes emitting light with remarkable high-efficiency in aqueous medium", *Tetrahedron Letters*, vol. 43, pp. 8955-8958 (2002).
Akhavan-Tafti et al., "A Novel Substitution Process for the Preparation of Alkoxy-, Aryloxy-, and Acyloxy-Substituted 1,2-Dioxetanes", *Journal of the American Chemical Society*, vol. 119, pp. 245-246, 1997.
Matsumoto et al., "3-(4-Acyl-3-hydroxyphenyl)-1,2-dioxetanes as a Chemiluminescent Substrate with High Efficiency in an Aqueous System", *Tetrahedron Letters*, vol. 37, No. 47, pp. 8535-8538, 1996.
Sawa et al., "Toward the Antibody-Catalyzed Chemiluminescence. Design and Synthesis of Hapten", *Bioorganic and Medicinal Chemistry Letters*, vol. 8, No. 6, pp. 647-652, Mar. 17, 1998.
Sabelle et al., "McMurry intermolecular cross-coupling between an ester and a ketone: scope and limitations", *Tetrahedron Letters*, vol. 43, No. 20, pp. 3645-3648, May 13, 2002.
Ohashi et al., "Intramolecular electron-transfer-induced cleavage of dioxetanes observed in fast-atom bombardment tandem mass spectrometry", *European Journal of Mass Spectrometry*, vol. 7, No. 6, pp. 441-445, 2001.
Sabelle et al., "Design and Synthesis of Chemiluminescent Probes for the Detection of Cholinesterase Activity", *Journal of the American Chemical Society*, vol. 124, No. 17, pp. 4874-4880, 2002.
Matsumoto, "Advance chemistry of dioxetane-based chemiluminescent substrates originating from bioluminescence", *Journal of Photochemistry and Photobiology*, vol. 5, pp. 27-53, 2004.

*Primary Examiner* — Janet L. Andres
*Assistant Examiner* — Raymond Covington
(74) *Attorney, Agent, or Firm* — Oliff & Berridge, PLC

(57) ABSTRACT

The invention concerns novel 1,2-dioxetane derivatives of general formula (I) as defined in the description, capable of emitting a detectable luminescent signal, their use in a method for detecting and/or quantizing a physical, chemical or biological, in particular enzymatic, phenomenon, as well as a kit for implementing said method.

23 Claims, No Drawings

LIGHT-EMITTING BIOMARKER

The present invention relates to novel compounds capable of emitting a detectable luminescent signal, to their use in a method for detecting and/or quantifying a physical, chemical or biological, especially enzymatic phenomenon, and also to a kit enabling the method to be implemented.

Numerous detection methods used in biochemistry, or in cellular biology, rely on the generation of a light signal, for example fluorescence.

Thus, numerous chromogenic, fluorescent or luminescent tests are described in vitro for detecting the activities of various enzymes. Most of these tests rely on the use of donor/acceptor or donor/quencher pairs for fluorescence resonance energy transfer (FRET) or the use of pro-fluorophore entities.

Unfortunately, this method of detection, satisfactory for in vitro analysis, does not generally prove workable for in vivo analysis.

Thus, for in vivo applications, it is necessary to supply an excitation in the near infrared. The choice of donor/acceptor or donor/quencher pairs for which the excitations do not overlap thus becomes extremely more limited (Funovics et al., Anal. Bioanal. Chem., 2003, 377:956-963).

In view of being free from this necessity to excite the fluorescence donor in the near infrared, it has been proposed to use bioluminescent or chemiluminescent compounds, that is to say whose luminescence is generated at the end of a chemical or biological reaction (Laxman et al., Proc. Natl. Acad. Sci. USA, 2002, 99:16551-16555).

Chemiluminescent compounds, their preparation and their use have been known for a long time. These so-called "high-energy" molecules contain sufficient energy to generate carbonyl groups in an excited electronic state, responsible for the chemiluminescence phenomenon observed.

As a representation of chemiluminescent compounds, mention may be made of compounds derived from dioxetane and more particularly the derivatives of 1,2-dioxetane. These compounds are thermally labile and can be decomposed over a wide temperature range while emitting a light signal. Generally, these compounds have the following general formula:

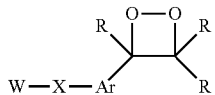

in which each R substituent corresponds to a hydrocarbon-based radical optionally comprising one or more heteroatoms, and two adjacent R groups or one R adjacent to Ar—X—W and one of the two other R groups or Ar may be linked, X may represent O, S or NH and W may represent a detachable group, where appropriate charged.

Numerous derivatives of 1,2-dioxetane have been synthesized, among which compounds comprising a spiroadamantyl radical bonded in position 3 are already used as chemiluminescent substrates. Such derivatives are especially described in documents WO 96/24849, WO 90/07511 and U.S. Pat. No. 5,330,900. These derivatives of 1,2-dioxetane may comprise a recognition site for an enzyme and may be activated by an enzyme recognizing this site in order to generate a luminescent signal.

More recently, other dioxetane derivatives have also been developed, described in JP 2002-02038, EP 1 342 724, and US 2004/0077018, in which various radicals were used to stabilize the dioxetane ring.

The principle of the chemiluminescence reaction of these compounds relies on an exchange of electrons (CIEEL, Chemically Induced Electron Exchange Luminescence) between the phenolate functional group and the strained dioxetane ring located at the para position of the phenol aromatic ring (Matsumoto, J. Photochem. Photobiol. C: Photochem. Rev., 2004, 5:27-53). The generation of an unstable compound comprising a phenolate leads to rupture of the strained 1,2-dioxetane unit, stabilized by the R radicals, following an electron exchange with the phenolate via the CIEEL phenomenon, resulting in the appearance of an activated ester that returns to the ground state by emitting a luminescent signal.

Phenol, by itself, and also its esters with carboxylic acids, are the most commonly used precursors for generating an oxygen anion (oxyanion) of phenol in an alkaline aqueous solution. However, other derivatives of this type have also been synthesized from 1,2-dioxetane in which the same oxygen atom has been replaced by a thiol group, an amine group or a carbon (Matsumoto, J. Photochem. Photobiol. C: Photochem. Rev., 2004, 5:27-53; Sabelle et al., J Am Chem Soc, 2002, 124(17); 4874-4880; Matsumoto et al., Tetrahedron Lett, 2004, 45: 3779-82; WO 96/24849; WO 00/44719). However, the latter derivatives have a substantially lower quantum yield and cannot be used in practice.

As for the present invention, it aims to provide novel compounds derived from 1,2-dioxetane capable of generating directly, or by intramolecular fluorescence resonance energy transfer (FRET), a luminescent signal capable of being detected through a thickness of layers of biological tissue.

Another object of the present invention is to provide compounds derived from 1,2-dioxetane which can be activated by any chemical, physical or biological phenomenon, and in particular an enzymatic activity. The invention thus has the advantage of expressing information resulting from this activation, for example information of hydrolysis type within the context of an enzymatic activity, into the appearance of a phenolate or a thiophenate, and in conferring on the derivatives spectroscopic properties distinct from those with which they were originally endowed.

Another object of the present invention is to provide compounds derived from 1,2-dioxetane capable of being administered in vivo in order to be able to be used in medical imaging methods.

The inventors have thus observed, against all expectations, that it was possible to combine with a 1,2-dioxetane type backbone, such as defined previously, a reactive branch that can be activated by a physical, chemical or biological phenomenon, and especially by an enzymatic activity, without being detrimental to the emission of a light signal.

The reactive branch in question according to the invention ensures, due to an intramolecular rearrangement, the transfer of electrons necessary for the activation of the light signal.

Thus, according to one of its first subjects, the present invention relates to a compound of general formula (I):

in which

S represents a labile structure that can be activated by a physical, chemical or biological phenomenon, B is a reactive branch, of which the chemical structure is such that the activation of the labile structure S induces its intramolecular rearrangement in a suitable form for releasing a molecule A⁻;

A is a chromophore of general formula (IIa):

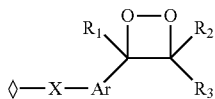

in which:
◇ symbolizes the covalent bond with B;
a) $R_1$, $R_2$ and $R_3$ represent, independently of one another, a radical as defined subsequently, such as for example a hydrogen atom, an alkyl radical, an alkoxy radical, an aryl radical, a hydroxyl radical, an oxo unit, an amino radical, a silyl radical, a halogen atom;
b) $R_2$ and $R_3$ may form an oxo unit;
c) $R_1$ and $R_2$ may be linked so as to form a ring fused with the dioxetane ring, as defined subsequently;
d) $R_2$ and $R_3$ or $R_1$ and Ar may be linked so as to form a spiroring with the carbon of the dioxetane entity which bears them, as defined subsequently;
Ar represents an arylene radical especially as defined subsequently; and
X represents O, NH or S,
and its derivatives, such as salts, esters or derivatives obtained by functionalization of a compound of general formula (I) with at least one unit intended for targeting.

According to another subject, the present invention relates to a compound of general formula (Va):

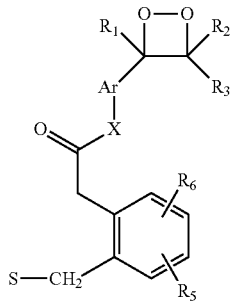

in which:
S represents a labile structure and X, Ar, $R_1$, $R_2$, $R_3$, $R_5$ and $R_6$ are as defined subsequently.

According to another of its subjects, the present invention relates to a compound deriving from the functionalization of a compound according to the invention with at least one structural unit favoring, for example, the targeting to a particular cell or tissue.

According to yet another of its subjects, the present invention relates to the use, for the purpose of detecting and/or quantifying a physical, chemical or biological phenomenon, of at least one compound according to the present invention, in which S represents a labile structure that can be activated by said phenomenon.

According to yet another subject, the present invention relates to the use of a compound according to the invention, and especially of general formula (Va), for preparing a pharmaceutical composition intended for implementing a diagnostic method in vivo.

According to yet another of its subjects, the present invention relates to a kit for the detection and/or quantification of a biological entity, especially an enzyme, comprising a compound of general formula (I), and in particular of general formula (Va), in which S represents a labile structure that can be activated by said biological entity to be detected and/or quantified.

According to yet another of its subjects, the present invention relates to a method for detecting and/or quantifying a biological entity, especially an enzyme, comprising at least the steps of:
bringing at least an effective amount of at least one compound of general formula (I), and in particular of general formula (Va), in which S represents a labile structure that can be activated by said biological entity, especially an enzyme, to be detected and/or quantified, into contact in a medium assumed to contain said biological entity; and
measuring the luminescent signal generated.

According to yet another of its subjects, the present invention relates to an in vivo diagnostic method, especially for medical imaging purposes, comprising the detection and/or quantification of a biological entity, especially an enzyme, by means of a compound of general formula (I), and especially of general formula (Va), in which S represents a labile structure that can be activated by said biological entity to be detected and/or quantified.

DEFINITIONS

In the meaning of the present invention, the expression "alkyl radical" is understood to mean a saturated or unsaturated, linear, branched or cyclic, fused or unfused hydrocarbon-based radical having 1 to 20 carbon atoms, preferably 2 to 12 carbon atoms and better still 3 to 6 carbon atoms and more particularly 4 carbon atoms, capable of being substituted by radicals as defined below.

By way of example, included in this definition are radicals such as methyl, ethyl, isopropyl, n-butyl, t-butyl, t-butylmethyl, n-propyl, pentyl, n-hexyl, 2-ethylbutyl, heptyl, octyl, nonyl, decyl, undecyl, dodecyl, tetradecyl, pentadecyl, hexadecyl, heptadecyl, octadecyl, nonadecyl or icosanyl radicals.

In the meaning of the present invention, the expression "cyclic alkyl radical" is understood to mean an alkylene ring having 4 to 10 carbon atoms, such as a cyclopropyl, cyclopentyl, cyclohexyl, cyclohexylmethyl or cycloheptyl ring.

The expression "polycyclic alkyl radical" is understood to mean a polycyclic alkylene having 4 to 20 carbon atoms, in particular 6 to 12 carbon atoms, optionally substituted by 1 to 10 radicals independently chosen from a $C_1$-$C_{10}$ alkyl radical, especially a $C_2$-$C_6$ alkyl radical, a $C_1$-$C_{10}$ alkoxy radical, especially a $C_2$-$C_6$ alkoxy radical, a $C_1$-$C_{10}$ alkylamino radical, especially a $C_2$-$C_6$, alkylamino radical, a $C_1$-$C_{10}$ alkylthio radical, especially a $C_2$-$C_6$ alkylthio radical, a halogen atom and a $C_1$-$C_{10}$ haloalkyl radical, especially a $C_2$-$C_6$, haloalkyl radical.

By way of example of a polycyclic radical suitable for implementing the invention, mention may be made of the adamantyl radical or the bicyclo[2.2.1]heptyl radical.

In the meaning of the present invention, the expression "alkoxy radical" is understood to mean a —OR radical in which the alkyl residue is a saturated or unsaturated, linear, branched or cyclic, fused or unfused hydrocarbon-based radical, as defined above.

Mention may be made, by way of example, of methoxy, ethoxy, propoxy, butoxy, n-butoxy, isobutoxy, sec-butoxy, n-pentoxy, isopentoxy, sec-pentoxy, t-pentoxy, hexyloxy, methoxyethoxy, methoxypropoxy, ethoxyethoxy, ethoxypropoxy groups and the like.

In the meaning of the present invention, the expression "acyl radical" is understood to mean a saturated or unsaturated, linear, branched or cyclic, fused or unfused hydrocarbon-based radical, comprising a C=O functional group and having from 1 to 20 carbon atoms, in particular from 2 to 12 carbon atoms and preferably from 3 to 6 carbon atoms and more particularly 4 carbon atoms, for example a formyl radical, an acetyl radical, a succinyl radical, a benzoyl radical, a 1-naphthoyl or 2-naphthoyl radical.

The hydrocarbon-based chain of the aforementioned radicals may be interrupted by one or more heteroatoms chosen from O, N and S, to form, for example, a heteroalkyl radical such as an alkyl ether radical, an alkyl ester radical or a heterocycle.

In the meaning of the present invention, the expression "heterocyclic radical" is understood to mean, for example and nonlimitingly, a furanyl radical, a thiophenyl radical, a pyrolyl radical, an oxazolyl radical, an isoxazolyl radical, a thiazolyl radical, an isothiazolyl radical, an imidazolyl radical, a pyrazolyl radical, a furazanyl radical, a pyranyl radical, a pyridinyl radical, a pyridadinyl radical, a pyrimidinyl radical, or a pyradinyl radical.

In the meaning of the present invention, the expression "aryl radical" is understood to mean an aromatic ring system comprising from 1 to 5 aromatic rings, optionally fused, having 6 to 30 carbon atoms, optionally 6 to 10 carbon atoms, optionally comprising one or more heteroatoms chosen from O, N and S.

By way of example of aryl radicals suitable for implementing the invention, it is possible to mention the phenyl radical, naphthyl radical, anthryl radical, and all the aromatic rings comprising one or more heteroatoms chosen from O, N and S, such as for example pyridine, thiophene, pyrrole, furan, quinoline. In the meaning of the present invention, the expression "arylene radical" is understood to mean an aryl radical, as defined previously, which is bivalent.

As examples of substituents capable of being used to substitute the aforementioned radicals, mention may be made of a hydroxyl radical, an oxo unit, a thio radical, an amino radical, a halogen atom, an alkyl radical, a carboxy radical, an acyl radical, an amido radical, an alkoxy radical, an alkylamino or dialkylamino radical, an alkylthio radical, a haloalkyl radical such as, for example, a perfluoroalkyl radical, an alkylsilyl, dialkylsilyl or trialkylsilyl radical, an alkylsiloxy, dialkylsiloxy or trialkylsiloxy radical, an aryl radical, as defined previously.

In the meaning of the present invention, the expression "halogen atom" is understood to mean an atom of F, Cl, Br or I. The halogen atoms advantageously used in the present invention are fluorine and chlorine.

In the meaning of the present invention, the expression "haloalkyl radical" is understood to mean an alkyl radical as defined previously, substituted by one or more halogen atoms such as defined previously, and especially, by way of nonlimiting example, a perfluoromethyl radical.

1,2-Dioxetane Derivatives

The compounds according to the present invention have the general formula (I):

$$S-B-A$$

and comprise its derivatives, such as salts, esters or functionalized derivatives with structural elements, especially for targeting purposes.

Reactive Branch B

In the general formula (I) for compounds according to the invention, B is different from a simple chemical bond and represents a hydrocarbon-based reactive branch of which the chemical structure is such that the activation of the labile structure S by a chemical, physical or biological phenomenon induces the intramolecular rearrangement of B in a suitable form for releasing a molecule $A^-$.

Advantageously, B is represented by a $C_1$-$C_8$, especially $C_2$-$C_6$, and in particular $C_3$-$C_4$ alkyl radical, optionally interrupted by a $C_6$-$C_{14}$, especially $C_6$-$C_{10}$ arylene radical and/or by one or more heteroatoms chosen from O, N, and S, and optionally substituted by one or more substituents as defined previously and especially chosen from a hydroxyl radical, an oxo unit, an amino radical, a halogen atom, an alkyl radical, an alkoxy radical, a carboxy radical, an alkylamino radical, a dialkylamino radical, an aryl radical and an aryloxy radical. Advantageously, the alkyl radical comprises two carbon atoms.

The arylene radical may also be substituted by one or more substituents as defined previously.

According to one embodiment variant, the arylene radical is chosen from a phenylene or naphthalene radical. In the phenylene radical, the positions of the two bonds of the radical may be in ortho, meta or para positions. Advantageously, they are in ortho positions.

According to one embodiment, the reactive branch B may be chosen from:

a benzylidene radical;

a □-N(CH$_3$)-(CH$_2$)$_2$-N(CH$_3$)-C(O)-◊ radical, in which □ and ◊ respectively symbolize the covalent bond with the labile structure S and the chromophore A; or a derivative represented by the general formula (III):

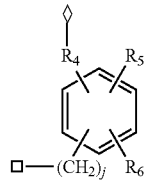

in which:

□ and ◊ symbolize, respectively, the covalent bond with the labile structure S and the chromophore A;

j is an integer ranging from 0 to 2, and advantageously is equal to 1;

$R_4$ is a $C_1$-$C_{20}$, especially $C_2$-$C_{12}$ and in particular $C_3$-$C_6$ hydrocarbon-based chain, where appropriate interrupted by one or more heteroatoms and/or —CO and/or —N(alkyl)-unit(s), placed ortho, meta or para to the □-CH$_2$)$_j$— radical, and especially chosen from the —(CH$_2$)$_k$-◊, —(CH$_2$)$_k$—C(O)-◊, —CH$_2$—O—C(O)—N(CH$_3$)—(CH$_2$)$_2$—N(CH$_3$)—C(O)-◊ radicals, with k being equal to 1 or 2, and advantageously equal to 1;

$R_5$ and $R_6$ are, independently of one another, a hydrogen atom or a saturated or unsaturated, linear, branched or cyclic, $C_1$-$C_{20}$, especially $C_2$-$C_{12}$ and in particular $C_3$-$C_6$ hydrocarbon-based chain chosen from an alkyl radical, an alkoxy radical, an alkylamino or dialkylamino radical, an alkylthio radical, or a $C_6$-$C_{30}$, especially $C_6$-$C_{10}$ aromatic ring chosen from an aryl radical, an aryloxy radical, an arylamino radical and an arylthio radical, especially as defined previously.

According to one particular embodiment, the radicals $R_5$ and $R_6$ are, independently of one another, chosen from:

a hydrogen atom, a $C_1$-$C_6$ alkyl radical, a $C_2$-$C_6$ alkenyl radical, a $C_3$-$C_6$ alkynyl radical, branched or unbranched, a $C_3$-$C_6$ cycloalkyl radical, substituted or not by one or more substituents as defined previously and especially chosen from a halogen atom, an alkyl radical, an alkoxy radical, an aryl radical such as, for example, a benzyloxy radical or a benzyl radical; and a $C_3$-$C_8$, in particular $C_4$-$C_7$ cyclic, aliphatic, aromatic or heteroaromatic hydrocarbon-based chain comprising one or more heteroatoms chosen from O, N and S, optionally substituted by one or more substituents as defined previously and especially chosen from a halogen atom, an alkyl radical, an alkoxy radical, and an aryl radical, such as, for example, a benzyloxy radical, a benzyl radical, a phenyl radical or a naphthyl radical.

According to one particular embodiment, when $R_4$ is chosen from $-(CH_2)_k-C(O)-\diamond$ and $-CH_2-O-C(O)-N(CH_3)-(CH_2)_2-N(CH_3)-C(O)-\diamond$, then $R_4$ is in the para position with the $O-(CH_2)_j-$ radical, $j=k=1$ and $R_5=R_6=H$.

According to another particular embodiment, $R_4$ may be represented by $-(CH_2)_k-\diamond$, positioned ortho to the $\square$-$CH_2)_j-$ radical, and $j=k=1$ and $R_5=R_6=-O-CH_3$.

Advantageously, the reactive branch B may be such as defined in U.S. Pat. No. 6,271,345, the content of which is incorporated here by reference.

According to one particular embodiment, the intramolecular rearrangement of B leads to the formation of a lactam or a lactone.

Chromophore A

In the general formula (I) for the compounds derived from 1,2-dioxetane according to the invention, the chromophore A is represented by the general formula (IIa):

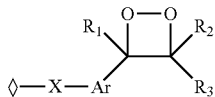

in which:
◇ symbolizes the covalent bond with B;
a) $R_1$, $R_2$ and $R_3$ represent, independently of one another, a hydrogen atom, a hydroxyl radical, an amino radical, a thio radical, a halogen atom, a $C_1$-$C_{20}$, especially $C_2$-$C_{12}$, and in particular $C_3$-$C_6$ hydrocarbon-based chain chosen from an alkoxy radical, an alkyl radical, a heteroalkyl radical, a cycloalkyl radical, a heterocycloalkyl radical, an ether radical, an alkenyl radical, an alkynyl radical, an alkylamino radical, a dialkylamino radical, an alkylsilyl, dialkylsilyl or trialkylsilyl radical, an alkylsiloxy, dialkylsiloxy or trialkylsiloxy radical, an alkylthio radical, a haloalkyl radical, a $C_6$-$C_{30}$, especially $C_6$-$C_{10}$ aromatic ring, chosen from an aryl radical and a heteroaryl radical, substituted where appropriate;
b) $R_2$ and $R_3$ may be together to form an oxo unit;
c) $R_1$ and $R_2$ may be linked so as to form a $C_4$-$C_8$ ring fused with the dioxetane ring, where appropriate interrupted by one or more heteroatoms chosen from O, N and S, and possibly being substituted by one or more radicals such as defined previously in a) for $R_1$, $R_2$ and $R_3$,
d) $R_2$ and $R_3$ or $R_1$ and Ar may be linked so as to form a $C_4$-$C_{20}$, especially $C_6$-$C_{10}$ spiro ring with the carbon of the dioxetane entity which bears them, this ring possibly being monocyclic or polycyclic, saturated or unsaturated, aromatic, fused or unfused, and where appropriate incorporating one or more heteroatoms chosen from O, N and S and optionally being substituted by one or more radicals such as defined previously in a) for $R_1$, $R_2$ and $R_3$;

Ar represents a $C_6$-$C_{30}$, especially $C_6$-$C_{10}$ arylene radical, optionally substituted by one or more substituents especially chosen from a hydroxyl radical, a halogen atom, an oxo unit, an amino radical, an alkylamino radical, a dialkylamino radical, a thio radical, an alkylsilyl, dialkylsilyl or trialkylsilyl radical, an alkylsiloxy, dialkylsiloxy or trialkylsiloxy radical, an alkyl radical, an alkoxy radical, an alkylthio radical, a carboxy radical, a formyl radical, an alkyl ester radical, an alkyl ketone radical, a haloalkyl radical, an aryl radical, an aryl ester radical, an aryl ketone radical, an arylamino radical, a diarylamino radical; and X may represent O, NH or S. Advantageously, X may represent O.

The compound $A^-$ generated following the activation of the labile structure S and the intramolecular rearrangement of the reactive branch B is unstable and reacts while emitting a light signal by means of a chemiluminescent reaction.

According to one particular embodiment, $R_1$ may be a fluorescent radical or an alkyl radical, as defined previously, substituted by a fluorescent radical.

According to another embodiment, Ar may be substituted by a radical that is fluorescent in itself, or a radical able to confer a fluorescent character to the whole of the structure or a radical able to modify the fluorescent properties thereof.

According to another particular embodiment, Ar and $R_1$ and/or $R_2$ and $R_3$ may be combined to form a cyclic or polycyclic or spiro-fused alkyl radical which may:
either comprise at least one double bond or at least one triple bond in the ring or in the side chain, and optionally one or more heteroatoms chosen from O, N and S;
or be joined to, or fused with, a substituted or unsubstituted aromatic ring. When Ar and $R_1$ are not bonded together, Ar may be an aryl radical, such as a phenyl, naphthyl, or anthryl radical, where appropriate substituted, especially by radicals as defined previously and $R_1$ may be as defined previously. Such compounds are described in greater detail in Application US 2004/0077018, the content of which is incorporated into the present application by reference.

According to another embodiment, $R_2$ and $R_3$ are bonded together to form an adamantyl radical in the spiro position of the carbon of the dioxetane ring which bears them, where appropriate substituted, especially by the $R_8$ and $R_9$ radicals defined below.

According to another embodiment, $R_1$ and $R_2$ may be bonded together to form a ring fused with the dioxetane ring, and comprising, optionally, one or more heteroatoms chosen from O, N and S. Advantageously, $R_1$ and $R_2$ form an oxocyclopentane fused with the dioxetane. Such compounds are especially described in Application EP 1 342 724, the content of which is also incorporated here by reference.

According to another embodiment, $R_1$ and $R_2$ may be bonded together to form a polycyclic ring system fused with the dioxetane. Such compounds are described in Application JP 2004-262817, the content of which is incorporated here by reference.

According to one particular embodiment variant, the chromophore A is represented by the general formula (IIb):

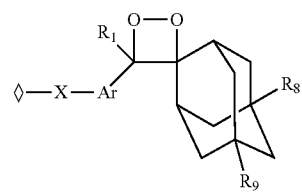

in which:
◊ symbolizes the covalent bond with B, and
$R_1$ is as defined previously. Advantageously, $R_1$ may be chosen from an alkyl radical, a fluorescent group and an alkyl radical substituted by a fluorescent group. The alkyl radical is as defined previously. Advantageously, $R_1$ may be a saturated or unsaturated, linear, branched or cyclic, $C_1$-$C_6$ alkyl or $C_1$-$C_6$ alkoxy radical optionally comprising one or more heteroatoms chosen from O, N and S, and optionally substituted. $R_1$ may be substituted by radicals as defined previously. Advantageously, $R_1$ is a $C_1$-$C_3$ alkyl or $C_1$-$C_3$ alkoxy radical, preferably a methyl or methoxy radical.

$R_8$ and $R_9$ are, independently of one another, a hydrogen atom or an electroactive radical;

X represents O, NH or S. Advantageously X represents 0; and

Ar represents an arylene radical, as defined previously, or a radical of general formula (IVa):

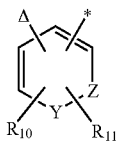

in which:
Δ symbolizes the covalent bond with X and * symbolizes the covalent bond with the dioxetane ring. Δ and * may be positioned in ortho, meta or para positions. Advantageously, Δ and * may be positioned in the meta position;

$R_{10}$ represents a hydrogen atom, an electroactive radical or a fluorescent radical. Advantageously, the electroactive radical may be capable of modifying the fluorescent properties of the Ar radical to the form, for example, of an alkylsilyl, dialkylsilyl or trialkylsilyl radical, an $NO_2$ radical, an anthryl radical, a naphthyl radical (for example, see Matsumoto et al., Tetrahedron Lett, 2002, 43: 8955-58);

$R_{11}$ is chosen from a hydrogen atom or represents an aryl radical, for example a $C_6$-$C_{10}$ aryl radical, fused with a phenylene radical, especially a phenyl radical to form a naphthylene radical.

In the meaning of the present invention, the expression "electroactive group" is understood to mean an electron-acceptor group or an electron-donor group.

According to one particular variant, the chromophore A is such that at least one of the groups $R_8$ or $R_9$ or $R_{10}$ is an electroactive radical that promotes the solubilization of the compound of general formula (I) according to the invention in an aqueous solution.

As examples of groups that promote the solubilization of the compound of general formula (I) in an aqueous solution, mention may be made of ammonium, phosphonium, sulfonium, carboxylic acid, sulfonic acid, trifluoromethylsulfonyl, methylsulfonyl, cyano and hydroxy radicals.

According to another embodiment, $R_8$ and $R_9$ are, independently of one another, an electroactive radical chosen from a hydroxyl radical, a halogen atom, a cyano radical, an amide radical, an alkoxy radical, a haloalkyl radical, a phenyl radical, an alkoxyphenyl radical.

According to yet another embodiment variant, $R_{10}$ is a hydrogen atom or an electroactive radical advantageously chosen from a halogen atom, especially a chlorine or fluorine atom, a cyano radical, a nitro radical, a monosubstituted or disubstituted amide radical, an alkyl radical, an alkoxy radical, a trialkylammonium radical, an alkylamido radical, an alkylcarbamoyl radical, an ester radical, an alkylsulfonamido radical, a trifluoromethyl radical, an alkylsilyl, dialkylsilyl or trialkylsilyl radical, an alkylsiloxy, dialkylsiloxy or trialkylsiloxy radical, an alkylaminosulfonyl radical, an alkylsulfonyl radical, an alkyl thioether radical, a haloalkyl radical, a $C_6$-$C_{10}$ radical chosen from an aryloxy radical, an arylamido radical, an arylcarbamoyl radical, an arylsulfonamido radical, an aryl radical, a heteroaryl radical, a triarylsilyl or alkylarylsilyl radical, a triarylsiloxy radical, an arylamidosulfonyl radical, an arylsulfonyl radical and an aryl thioether radical.

According to one particular embodiment, $R_8$, $R_9$ and $R_{10}$ are advantageously a hydrogen atom.

According to another particular embodiment, $R_1$ or $R_{10}$ may be a fluorescent radical in order to modify, by intramolecular FRET, the emission wavelength of the luminescent compound according to the invention.

For example, these fluorescent radicals may be chosen, nonlimitingly, from phenyl and its derivatives, naphthalene and its derivatives such as 5-dimethylaminonaphthalene-1-sulfonic acid and hydroxynaphthalenes, anthracene and its derivatives such as 9,10-diphenylanthracene and 9-methylanthracene, pyrene and its derivatives such as N-(1-pyrene) iodoacetamide and hydroxypyrenes, biphenyl and its derivatives, acridine and its derivatives such as hydroxyacridines and 9-methylacridine, coumarin and its derivatives such as 7-dialkylamino-4-methylcoumarin and 4-bromomethyl-7-methoxycoumarin, xanthene and its derivatives, phthalocyanine and its derivatives, stilbene and its derivatives such as 6,6'-dibromostilbene and hydroxystilbenes, furan and its derivatives, oxazole and its derivatives, oxadiazole and its derivatives, nitrobenzoxadiazole and its derivatives such as hydroxynitrobenzoxadiazoles, benzothiazole and its derivatives, fluorescein and its derivatives such as 5-iodoacetamidofluorescein and fluorescein-5-maleimide, rhodamine and its derivatives such as tetramethylrhodamine, tetraethylrhodamine and rhodols, BODIPY and its derivatives, eosin and its derivatives, erythrosine and its derivatives such as hydroxyerythrosines and 5-iodoacetamidoerythrosine, resorufin and its derivatives such as hydroxyresorufins, quinoline and its derivatives such as 6-hydroxyquinoline and 6-aminoquinoline, carbazole and its derivatives such as N-methylcarbazole, fluorescent cyanines and derivatives such as hydroxycyanines, carbocyanine and its derivatives such as phenylcarbocyanine, pyridinium salts and derivatives such as 4-(4-dialkyldiamidostyryl)-N-methylpyridinium iodate, a fluorescent complex of lanthanides and its derivatives, fluorescent proteins such as Green Fluorescent Protein (GFP) and its mutants and quantum dots.

Advantageously, $R_1$ and $R_{10}$ may advantageously be chosen from molecules of which the fluorescence emission wavelength is in the range from 400 to 900 nanometers, especially from 500 to 900, and more particularly from 600 to 900 nanometers, such as for example rhodamine and its derivatives, BODIPY and its derivatives, cyanines and derivatives or quantum dots.

According to another particular embodiment, the compounds according to the present invention may be of general formula (Va):

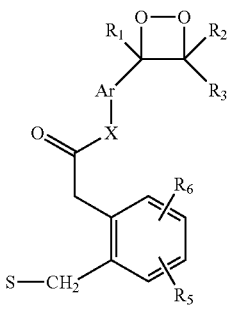

in which:

S represents a labile structure, and X, Ar, $R_1$, $R_2$, $R_3$, $R_5$ and $R_6$ are as defined previously.

Advantageously, $R_2$ and $R_3$ are linked to form a spiro adamantyl radical with the carbon of the dioxetane ring which bears them, where appropriate substituted by radicals such as defined previously, especially by radicals such as $R_8$ and $R_9$.

Advantageously, $R_1$, $R_5$ and $R_6$ are methoxy radicals.

According to another particular embodiment, the compounds according to the present invention may be of general formula (Vb):

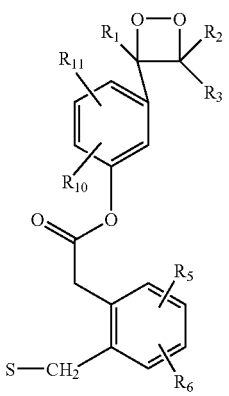

in which:

S represents a labile structure, and Ar, $R_1$, $R_2$, $R_3$, $R_5$, $R_6$, $R_{10}$ and $R_{11}$ are as defined previously.

Advantageously, $R_2$ and $R_3$ are fused to form a spiro adamantyl radical position with the carbon of the dioxetane ring which bears them, where appropriate substituted by radicals such as defined previously, especially by radicals such as $R_8$ and $R_9$.

Advantageously, $R_1$, $R_5$ and $R_6$ are methoxy radicals.

$R_{10}$ and $R_{11}$ are advantageously a hydrogen atom, or $R_{10}$ is a hydrogen atom and $R_{11}$ forms a naphthylene radical with the phenylene radical.

According to another particular embodiment, the compounds according to the present invention may be of general formula (Vc):

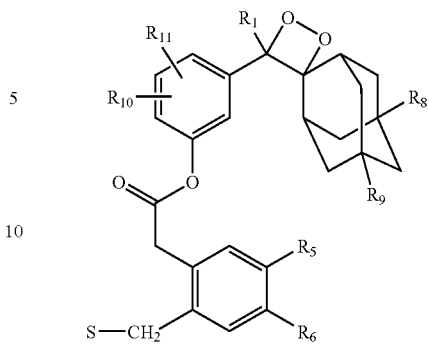

in which S represents the labile structure and $R_1$, $R_5$, $R_6$, $R_8$, $R_9$, $R_{10}$ and $R_{11}$ are as defined previously.

According to another particular embodiment, the compounds according to the present invention may be represented by the general formula (Vc) in which $R_8=R_9=R_{10}=R_{11}=H$ and $R_{11}=R_5=R_6=-O-CH_3$.

Labile Structure S

In the general formula (I) of the compounds according to the invention, S represents a labile structure that can be activated by a chemical, physical or biological phenomenon or entity.

The expression "physical phenomenon" is understood in the meaning of the present invention to denote, for example, a temperature variation or a pressure variation.

The expression "chemical phenomenon" is understood in the meaning of the present invention to denote a phenomenon involving a chemical entity modifying the chemical properties of the surroundings, such as for example a variation of pH via an increase or decrease in protons, a variation in the salinity via an increase or decrease in the content of salt(s), a variation in the redox potential, the appearance or disappearance of chemical species, for example ions such as $F^-$, $S^-$, and alkaline-earth metal ions such as $Ca^{2+}$.

When S represents a labile structure that can be activated by a chemical phenomenon, S may advantageously be, for example, an ammonium, amide, amine, ester, silylane, thiol, carbamate or carbonate group.

The expression "biological phenomenon" is understood in the meaning of the present invention to denote a phenomenon involving the activity of a biological entity, for example an enzymatic activity, in the form, for example, of a hydrolysis, transfer of an amine group, or isomerization.

Thus, during the activation of the compounds according to the invention by a biological phenomenon, the compounds are subjected to the action of a biological entity.

By way of illustration of a biological entity capable of activating the compounds according to the invention, mention may be made, nonlimitingly, of enzymes, ribozymes and abzymes.

By way of example of enzymes capable of activating the compounds according to the invention, mention may be made of transferases, such as aminotransferases; hydrolases such as esterases (for example alkaline phosphatase), glucosidases, proteases (for example trypsin, metalloproteinases or caspases); isomerases.

When S is a structure that can be activated by a biological entity, S may advantageously be of general formula (VI):

P-L-☐ in which:
□ symbolizes the covalent bond with B;
P represents a substrate that can be recognized by said entity; and
L represents an oxygen, sulfur, nitro unit, carbonyl or a —CO-Q- functional group, with Q being O, S or NH.

According to one embodiment, S may represent a structure that is labile by action of an enzyme, and especially by action of a hydrolase.

Advantageously, when S represents a structure that is labile by action of a protease-type hydrolase, L represents —CO-Q, with Q being NH, and P represents a substrate recognized by a protease, such as for example a peptide or pseudopeptide residue.

By way of example of proteases likely to be suitable for implementing the present invention, mention may be made, nonlimitingly, of caspases such as 1a caspase-3, acylaminoacyl peptidase, aminopeptidase M, penicillin G acylase, thermolysin, cathepsins B, G, L, metalloproteinases, elastase, subtilisin, plasminogen activator and urokinase.

According to one embodiment, when P is a peptide residue, it comprises at least two amino acid residues, in particular at least four, in particular at least six and, more particularly at least eight amino acid residues.

These amino acids may be natural or synthetic and in L or D configuration.

These peptides may be obtained by chemical synthesis or molecular biology according to the usual methods of a person skilled in the art.

By way of example of a peptide residue suitable for implementing the present invention, mention may be made of the DEVD tetrapeptide sequence (amino acid written in single-letter code) which is selectively hydrolyzed from the latter aspartate residue by the caspase-3.

According to another embodiment variant, S may represent a structure that is labile by action of an esterase-type hydrolase, such as a carboxyesterase, a phosphatase or a lipase.

In this case, L may represent —CO-Q with Q being O, and P representing a carbon-based residue (of alkyl chain type so that the P-L assembly forms a residue of a carboxylic acid, especially of a fatty acid) recognized by an enzyme of esterase or glucosidase type, or a phosphate group recognized by a phosphatase-type enzyme.

When P is a phosphate group, it may be of formula (VII)

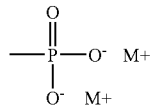

in which M$^+$ represents a cation such as an alkali metal, such as Na$^+$ or K$^+$, an ammonium, or a quaternary ammonium cation N(R)$_4^+$ in which each R may be a C$_1$-C$_2$ alkyl, an arylalkyl, such as a benzyl, or form part of a heterocycle, such as a pyridinium ring.

Such structures are advantageously hydrolyzed by an alkaline phosphatase.

According to another embodiment variant, S may represent a structure that is labile by action of a glucosidase-type enzyme.

In this case, L may advantageously be an oxygen atom and P represents a substrate recognized by a glucosidase, such as a sugar.

By way of example of a sugar likely to be suitable for implementing the invention, mention may be made of α-D- or β-D-galactoside, α-D- or β-D-glucoside, α-D- or β-D-mannoside and α-D- or β-D-fructofuranoside.

According to another embodiment, S may represent a structure that is labile by action of an aminotransferase.

In this case, L may represent a carbonyl group and P may represent a substrate recognized by an enzyme such as, for example and nonlimitingly, an alanine aminotransferase or an aspartate aminotransferase.

Targeting

According to one embodiment, a compound according to the invention may comprise, in addition, at the labile structure S, a target structure D.

Thus, a compound may be of general formula (VII) below:

$$D\text{-}S\text{—}B\text{-}A$$

in which:
D represents a target structure; and
S, B and A are as defined previously.

The target structure D, or ligand, is an element that can of recognize or preferentially bond to cells expressing a particular cellular element, such as for example, and nonlimitingly, a receptor, an enzyme, a structural protein, a glycoprotein, a sugar, a lipid or a phospholipid. Advantageously, the cellular element is a membrane element, preferably having one part of its structure positioned in the extracellular medium.

According to one embodiment, this cellular element may be specific to a physiological or pathological state of the cell or of the tissue surrounding the cell or of the organ comprising the cell. Thus, and nonlimitingly, the cellular element may be specific to the growth state of the cell, the position in the cell cycle, an inflammatory response of the cell or of the tissue, apoptosis, or tissue degeneration.

The expression "recognize or preferentially bond to" aims to indicate that the target structure D has a particular affinity for the cells or tissues in question, even though a nonspecific or less important bond with other cells or other tissues cannot be completely excluded in vivo or ex vivo. The preferential bond however makes it possible to target the compounds according to the invention at sites of interest, reducing the dissemination of the compound according to the invention to tissues and/or cells of less interest.

Thus, the target structure D may be chosen, for example and nonlimitingly, from a lectin, an antibody or a fragment of the latter that recognizes an element present on the surface of the cells such as for example a protein, a sugar or a lipid; a cell receptor ligand such as, for example, a peptide such as the neuropeptide Y, a catecholamine such as adrenalin, an antagonist such as, for example, a β-adrenergic receptor antagonist such as propranolol, a growth factor, an aminoacid or a derivative of the latter such as, for example, glutamate, a cytokine such as, for example, an interleukin, an interferon or a TNF, a hormone, a vitamin, an apoliproprotein or cholesterol; a ligand capable of interacting with a membrane lipid or phospholipid such as, for example, an annexin; a ligand capable of interacting with a sugar present at the surface of the cells.

The expression "cell receptor" is understood to mean any cellular element capable of transducing information from the outside to the inside of the cell.

It is a matter for the knowledge of the person skilled in the art to determine the nature of the structure D suitable for the desired targeting, where appropriate by making use of test methods commonly practiced in the field.

According to one embodiment, the target structure D may be a ligand, for example a polypeptide, capable of bonding to the surface of cells present in a characteristic or specific way in a particular tissue or that present a pathology.

The target structure D may also bond to the surface of tumor cells or cells present in a tumor tissue, or to the surface of cells present in an inflammatory tissue.

The target structure D may, for example, bond to the surface of cells engaged in an apoptosis process, which expose, on their surface, negatively charged lipids, such as for example phosphatidylserine.

According to one embodiment variant, the target structure D may be a protein or a protein fragment such as a peptide or a polypeptide or a pseudopeptide.

Among the proteins capable of bonding to the membranes exposing negatively charged lipids, mention may be made, nonlimitingly, of the annexin family, the families of proteins comprising a C1 or C2 domain, such as factors V and VIII for blood coagulation, the families of proteins comprising a PH domain or a FYVE domain, or else the proteins comprising a domain identical or homologous to the 5 domain of β2-glycoproteins-I (βGP-I). These proteins or these domains derived from their sequences may be used as a target structure in compounds according to the invention.

According to another embodiment, one or more compounds of general formula (I) may be fixed to a target structure D in order to increase, in particular, the intensity of the signal emitted.

Thus, at least one, especially at least two, in particular at least 3, in particular at least 4, and more particularly at least 5 compounds of formula S—B-A may be fixed to the target element D.

Detection Method

As specified previously, another subject of the present invention is the use, for the purpose of detecting and/or quantifying a chemical, physical or biological phenomenon, as specified previously, of at least one compound according to the invention, in which S represents a labile structure that can be activated by said phenomenon.

Advantageously, the compound according to the invention implemented in this use may be of general formula (Va) or (Vb) as defined previously.

In particular, the present invention aims to also provide a method for detecting and/or quantifying a biological entity.

The method according to the invention comprises at least the steps of bringing at least an effective amount of at least one compound according to the present invention, and especially of general formula (Va) or (Vb) in which S represents a labile structure that can be activated by said biological entity to be detected and/or quantified, into contact with a medium assumed to comprise said entity, and measuring of the luminescent signal generated.

The method according to the invention may be carried out in vitro, ex vivo or in vivo.

When a medium, in which a chemical, physical or biological phenomenon is able to occur, is brought together with an effective amount of at least one compound according to the invention of which the entity S represents a labile structure that can be activated by said phenomenon, under suitable conditions for achieving said phenomenon, the activation of the structure S leads to the emission of a luminescent signal.

By detecting the presence or absence of the luminescent signal, it is possible to demonstrate the presence or absence of said phenomenon and by measuring the intensity of the signal, the extent of the phenomenon can also be determined.

According to one particular embodiment, the biological phenomenon to be detected/quantified may be activity of a biological entity, especially an enzyme.

In this particular implementation, the labile structure S represents a substrate recognized by said enzyme. The action of the enzyme on the substrate S, especially on the group L of the general formula (II), under conditions suitable for the reactivity of the enzyme leads to the emission of a luminescent signal.

Thus, within the context, for example, of a hydrolase, the hydrolysis of an enzymatically hydrolyzable group, especially represented by L in the general formula (II), under suitable conditions for the reactivity of the enzyme, leads to the emission of a luminescent signal.

By detecting the presence or absence of a luminous signal, it is possible to demonstrate the presence or absence of the enzyme and by measuring the intensity of the signal, the concentration and/or the kinetic characteristics may also be determined.

Advantageously, the medium which may be suitable for implementing the method according to the present invention may be a synthetic or natural biological medium in the form of a sample of biological fluid.

It may be advantageous to use, in vitro, or where appropriate ex vivo, together with a compound according to the invention, at least one light amplifier capable of increasing the luminescent signal resulting from the degradation of said compound according to the invention.

Such compounds are already known.

By way of example of these amplifiers, mention may be made of fluorescein, bovine albumin, human albumin, polymeric quaternary onium salts such as poly(vinylbenzyltrimethyl)ammonium chloride (TMQ), poly(vinylbenzyltributyl)ammonium chloride (TBQ) (Sapphire-II™), poly(vinylbenzyldimethyl)ammonium chloride (BDMQ) (Sapphire-I™), poly(vinylbenzyltributyl)phosphonium chloride, poly(vinylbenzyltributyl)sulfonium chloride, poly(benzyldimethylvinylbenzyl)ammonium chloride, a sodium salt of fluorescein (Emerald™), poly(benzyltributyl)ammonium and the sodium salt of fluorescein (Emerald II™).

When the method according to the invention is carried out in vitro, the detection of the fluorescent signal may be made by any machine normally used by persons skilled in the art in this field.

For example, a sample brought into contact with a compound according to the C invention may, optionally after a period of incubation, be subjected to an analytical method comprising, or not, a step of separating the elements that make up the sample, for example by chromatography (for example, high performance liquid chromatography, HPLC) and a step of spectral analysis (for example, by UV spectroscopy) of the various fractions from the separation step. The detection and measurement of the spectroscopic signal specific to a compound according to the invention (for example, the height and the surface area of a chromatographic peak) may be correlated to the presence and/or to the intensity/amount of the phenomenon to be detected, such as for example the presence, amount and/or kinetic activity of an enzyme.

The method, and the use, according to the present invention may also be advantageously carried out in vivo.

The compounds according to the present invention may be first administered to a living organism, such as for example an animal or a human being, then the detection of the fluorescent signal may be carried out in vivo according to the methods usually employed in this domain.

Advantageously, the in vivo implementation of a use according to the invention makes it possible to establish images of susceptible tissues or organs in which said phenomenon to be detected/quantified is capable of occurring.

According to one particular embodiment, it is possible to establish images of the tissues or organs capable of expressing a biological entity, and especially an enzyme, to be detected and/or quantified.

Thus, according to one particular embodiment, the method according to the invention may be implemented in medical imaging methods.

According to another embodiment, the method according to the invention is an in vivo diagnostic method comprising the detection and/or quantification of a biological entity, especially an enzyme, by means of a compound of general formula (Va) or (Vb) in which S represents a labile structure that can be activated by said biological entity to be detected and/or quantified.

The method according to the invention may be applied, for example and non-exhaustively, for medical, experimental, clinical or preclinical diagnostic purposes in human beings or in animals such as laboratory animals or animals used in agriculture, such as rats, mice, guinea pigs, nonhuman primates, or pigs.

According to one particular embodiment, the biological entity capable of being detected and/or quantified by a method according to the invention may be an enzyme, chosen especially and nonlimitingly from an aminotransferase or a hydrolase, such as an esterase, a protease or a glucosidase.

According to another embodiment, when the enzyme to be detected and/or to be quantified is a protease, it may advantageously be chosen, nonlimitingly, from caspases, penicillinases, carboxypeptidases, trypsin, acylaminoacylpeptidase, aminopeptidases, cathepsins, metalloproteinases, elastase, subtilisin, thermolysin, plasminogen activator, urokinase and isomerases.

Within the context of in vivo implementation, the compounds according to the invention may be formed so as to be suitable for oral, or parenteral, especially intravenous, intraarterial, intracardial, intracerebroventricular, intraperitoneal, or intratumoral administration, or for pulmonary, nasal, ophthalmic and optionally rectal, vaginal or topical administration.

The compounds according to the invention may thus be used in a formulation suitable for the method of detection to be carried out and for the chosen administration route.

For example, the compounds according to the invention may be prepared in the form of a tablet, a gel capsule or a concentrated or unconcentrated aqueous solution. This aqueous solution may advantageously be sterile.

According to another embodiment, the compounds according to the invention may be in solid form, for example in powder form, and may be prepared in advantageously sterile aqueous solution just before their administration.

Thus, according to one of its aspects, the present invention also relates to the use of a compound according to the invention, especially of general formula (Va) or (Vb) for manufacturing a pharmaceutical composition intended for implementing an in vivo diagnostic method, especially a medical imaging method.

Thus, according to another of its aspects, the present invention also relates to a pharmaceutical composition comprising at least an effective amount of at least one compound according to the present invention, especially of general formula (Va) or (Vb).

Advantageously, the use of a compound according to the invention for preparing a pharmaceutical composition may take place in the form of a derivative, such as a pharmaceutically acceptable salt or ester. Thus, the present invention also relates to the salts and esters of the compounds according to the invention. By way of example of an ester of a compound according to the invention, mention may be made of a succinate, a hemisuccinate, a malate, a tartrate, or a glycolate of a compound according to the invention. By way of example of a salt of a compound according to the invention, mention may be made of a sulfate, a phosphate, a sodium salt, or a calcium salt of a compound according to the invention.

The adjustment of the appropriate effective amounts of the compound or compounds according to the invention to be used in a method or a use according to the invention, depends on the phenomenon, or on the entity, to be detected/quantified (chemical, physical or biological phenomenon) and on the environment in which the method according to the invention is carried out (in vitro, ex vivo or in vivo).

In vivo, the effective amounts may also be adjusted depending on the size and the weight of the individual to whom the method according to the invention is applied or with whom the use according to the invention is carried out, and also depending on the targeted organ or tissue.

The adjustments may be carried out by any methods normally used by a person skilled in the art.

In the meaning of the present invention, the expression "effective amount" is understood to mean the amount that is necessary and sufficient to obtain the desired effect, namely the detection and/or quantification of a chemical, physical or biological phenomenon, or of a biological entity.

According to another particular embodiment, the present invention relates to a kit for the detection and/or quantification, by generation of a luminescent signal, of a chemical, physical or biological phenomenon, said kit comprising at least one compound according to the present invention in which S represents a labile structure that can be activated by said physical, chemical or biological phenomenon to be detected and/or quantified.

According to one particular embodiment, the present invention relates to a kit for the detection and/or quantification of a biological entity, especially an enzyme, comprising a compound according to the present invention, and especially of general formula (Va) or (Vb), in which S represents a labile structure that can be activated by said biological entity to be detected and/or quantified.

According to one particular implementation, the kit according to the present invention may also comprise at least one light amplifier such as defined previously.

The present invention will be better understood from the following examples.

These examples are given as illustrations of the invention and must not be interpreted as limiting the scope of the present invention.

EXPERIMENTAL SECTION

Separation by High Performance Liquid Chromatography (HPLC)

Several chromatographic systems were used for the analytical experiments and the purification steps:

System A: reverse phase HPLC (C18, HYPERSIL GOLD, 5 is, 4.6×150) in a triethylammonium acetate buffer and acetonitrile (TEAA 100 mm, pH 7.0) [75% TEAA (2 min), then linear gradient from 25 to 100% (30 min) of acetonitrile] at a flowrate of 1.0 m/min. Double UV detection was carried out at 254 and 285 nm.

System B: reverse phase HPLC (C18, NUCLEOSIL, 5µ, 10×250) in a mixture of demineralized water and acetonitrile [75% water (5 min), then linear gradient from 25 to 55% (15 min) and from 55 to 90% (70 min) of acetonitrile] at a flowrate of 5.0 m/min. uV detection was carried out at 260 mm.

System C: reverse phase HPLC (C18, HYPERSIL GOLD, 5μ, 4.6×150) in a triethylammonium acetate buffer and acetonitrile (TEAA 100 mm, pH 7.0) [90% TEAA (2 min), then linear gradient from 10 to 90% (40 min) of acetonitrile] at a flowrate of 1.0 ml/min. Double UV detection was carried out at 254 and 285 mm.

Example 1

Reactive Branch

Synthesis of 4,5-dimethoxy-2-[(phenylacetamino) methyl]phenylacetic acid (7)

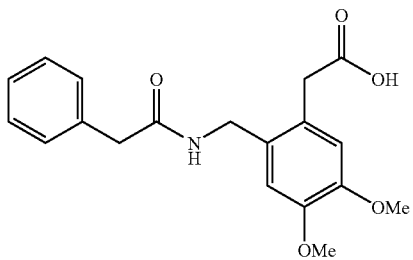

(7)

Finely pulverized potassium hydroxide (2 g, 36 mmol) was added to a solution of phenylacetonitrile 13 (2 ml, 17 mmol) in tert-butyl alcohol (20 ml) with stirring. The reaction mixture was refluxed for 45 min, then cooled to ambient temperature and poured into an aqueous solution of sodium chloride (50 ml). The product was extracted by chloroform ($CHCl_3$). The organic phase was dried over $MgSO_4$ and concentrated under reduced pressure to give phenylacetamide 12 (2.1 g, 94%) in the form of a white powder. M.p.=152° C. $^1$H NMR ($CDCl_3$, 300 MHz) δ 7.40-7.10 (m, 5H), 5.88 and 5.39 (br s, $NH_2$), 3.50 (s, 2H). $^{13}$C NMR ($CDCl_3$, 75 MHz) δ 173.8, 134.9, 129.5, 129.1, 127.5, 43.4.

A mixture of phenylacetamide 12 (2 g, 15 mmol) in a solution of potassium carbonate (4%, 2 ml, 0.6 mmol) and an aqueous solution of formaldehyde (37%, 2 ml, 20 mmol) was refluxed for 15 min (until completely dissolved). The mixture was cooled and extracted with $CH_2Cl_2$ (2×30 ml). The combined organic phases were dried over $MgSO_4$ and were concentrated under reduced pressure to give a crude product (1.35 g), recrystallization in toluene (20 ml) gave N-hydroxymethylphenylacetamide 11 (1.1 g, 44%) in the form of a white powder. M.p. 78° C. $^1$H NMR ($CDCl_3$, 300 MHz) δ 7.50-7.20 (m, 5H), 6.48 (br s, NH), 4.69 (t, J=7.0 Hz, 2H), 3.67 (t, J=7 Hz, OH), 3.60 (s, 2H). $^{13}$C NMR ($CDCl_3$, 75 MHz) δ 172.9, 134.4, 129.5, 129.0, 127.5, 64.2, 43.6.

A solution of homovanillic acid 10 (2 g, 11 mmol) and sulfuric acid (500 ml, 9.4 mmol) in methanol (100 ml) was refluxed for 3 hours. After cooling, a sodium bicarbonate solution was added to the reaction mixture. The product was extracted with $CH_2Cl_2$ (2×50 ml). The combined organic phases were dried over $MgSO_4$ and concentrated under reduced pressure to give methyl 4-hydroxy-3-methoxyphenylacetate 9 (2 g, 94%) in the form of a colorless oil. $^1$H NMR ($CDCl_3$, 300 MHz) δ 7.00-6.70 (m, 3H), 5.82 (br s, OH), 3.87 (s, 3H), 3.70 (s, 3H), 3.56 (s, 2H). $^{13}$C NMR ($CDCl_3$, 75 MHz) δ 172.6, 146.6, 144.8, 125.7, 122.1, 114.5, 111.8, 55.9, 52.1, 40.8.

Cesium carbonate (6.6 g, 20.2 mmol) and dimethyl sulfate (2 ml, 21 mmol) were added to a solution of methyl 4-hydroxy-3-methoxyphenylacetate 9 (2 g, 10.2 mmol) in anhydrous DMF (80 ml). The reaction mixture was heated at 90° C. for 3 hours. After cooling, water (20 ml) was added to the mixture and the product was extracted with diethyl ether (2×50 ml).

The combined organic phases were washed with an aqueous solution of NaCl (20 ml), dried over $MgSO_4$ and concentrated under reduced pressure. Chromatography on a silica gel using cyclohexane/ethyl acetate (1/1) as eluent mixture gave methyl 2-(3,4-dimethoxyphenyl)acetate 8 (1.7 g, 80%) in the form of a colorless oil. $^1$H NMR ($CDCl_3$, 300 MHz) δ 6.80-6.50 (m, 3H), 3.71 (s, 3H), 3.69 (s, 3H), 3.40 (s, 2H). $^{13}$C NMR ($CDCl_3$, 75 MHz) δ 172.2, 148.8, 148.0, 126.4, 121.3, 112.3, 111.1, 55.8, 55.7, 51.9, 40.6.

A precooled solution of acetic acid (20 ml) and sulfuric acid (730 μl, 14 mmol) was added to a mixture of N-hydroxymethylphenylacetamide 11 and methyl 2-(3,4-dimethoxyphenyl)acetate 8 (1.5 g, 7.2 mmol). The suspension was stirred for 2 hours at 0° C. then at ambient temperature for 12 hours. The reaction mixture was neutralized with a 5M sodium hydroxide solution at 0° C. The product was extracted with ethyl acetate (2×30 ml). The combined organic phases were dried over $MgSO_4$ and concentrated to give methyl 4,5-dimethoxy-2-[(phenylacetamino) methyl]phenylacetate 6 (2 g, 78%) in the form of a colorless oil which crystallized. M.p.=118° C. $^1$H NMR ($CDCl_3$, 300 MHz) δ 7.40-7.15 (m, 5H), 6.68 (s, 1H), 6.59 (s, 1H), 6.24 (br s, NH), 4.28 (d, J=5.6 Hz, 2H), 3.76 (s, 3H), 3.71 (s, 3H), 3.57 (s, 3H), 3.51 (s, 2H), 3.47 (s, 2H). $^{13}$C NMR ($CDCl_3$, 75 MHz) δ 172.8, 170.8, 148.4 (2C), 135.0, 129.7 (2C), 129.2, 127.5 (2C), 124.9, 113.8, 113.2, 56.3 (2C), 52.7, 44.2, 41.7, 38.3. IR ($CHCl_3$) 3017, 1732, 1660, 1520, 1466, 1275. Analysis calculated for $C_{20}H_{23}NO_5$: C=67.21, H=6.49 and N=3.92. Analysis measured: C=66.88, H=6.56, N=3.97.

An aqueous solution of lithium hydroxide (0.5 M, 56 ml, 28 mmol) was added to a solution of methyl 4,5-dimethoxy-2-[(phenylacetamino)methyl]phenylacetate 6 (2 g, 5.6 mmol) in methanol (50 ml). The reaction mixture was stirred at ambient temperature for 12 hours, then neutralized with an aqueous solution of HCl (2N) and precipitation of the product was observed. Filtration gave the 4,5-dimethoxy-2-[(phenylacetamino)methyl]-phenylacetic acid 7 (1.5 g, 78%) in the form of a white powder. M.p.=186° C. $^1$H NMR (($CD_3$)$_2$SO, 300 MHz) δ 8.40 (br s, 1H), 7.30-7.20 (m, 6H), 6.80 (s, 1H), 6.73 (s, 1H), 4.18 (d, J=5.6 Hz, 2H), 3.70 (s, 3H), 3.59 (s, 3H), 3.55 (s, 2H), 3.44 (s, 2H). $^{13}$C NMR (($CD_3$)$_2$SO, 75 MHz) δ 172.8, 170.0, 147.4, 147.3, 136.6, 129.9, 129.0 (2C), 128.3 (2C), 126.4, 125.2, 114.6, 111.9, 55.6, 55.4, 42.5, 39.6, 37.5. Analysis calculated for $C_{19}H_{21}NO_5$: C=66.46, H=6.16 and N=4.08. Analysis measured: C=66.52, H=5.92 and N=4.06.

Example 2

Dioxetane Precursor

Synthesis of 2-[1-(3-hydroxy)phenyl)-1-methoxymethylene]tricyclo[3.3.1.1$^{3,7}$]-decane (3a)

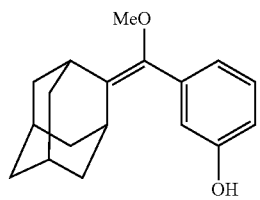

(3a)

tert-Butyldimethylsilyl chloride (2.7 g, 18 mmol) was added to a solution of methyl 3-hydroxybenzoate 4a (2.3 g, 15 mmol) and imidazole (2.6 g, 37.5 mmol) in anhydrous DMF (5 ml). The reaction mixture was stirred at ambient temperature for 14 hours under an argon atmosphere. The mixture was diluted with water (20 ml) and the product was extracted with n-pentane (2×20 ml). The combined organic phases were dried over MgSO$_4$ and concentrated under reduced pressure. Chromatography on silica gel using cyclohexane/ethyl acetate (v/v:95/5) as eluent mixture gave the methyl and 3-(tert-butyldimethylsilyloxy)benzoic acid ester 4b (3.7 g, 93%). $^1$H NMR (CDCl$_3$, 300 MHz) δ 7.42 (d, J=8 Hz, 1H), 7.28 (t, J=2 Hz, 1H), 7.07 (t, J=8 Hz, 1H), 6.81 (dd, J=8 Hz, 2 Hz, 1H), 3.68 (s, 3H), 0.78 (s, 9H), 0.1 (s, 6H). $^{13}$C NMR (CDCl$_3$, 75 MHz) δ 166.9, 155.8, 131.6, 129.4, 124.9, 122.7, 121.1, 52.2, 25.7, 18.2, −4.4.

LiAlH$_4$ (800 mg) was slowly added to a suspension of TiCl$_3$ (THF)$_3$ (16.5 g, 44.6 mmol) in anhydrous THF (15 ml) at 0° C. After 10 minutes at 0° C., triethylamine (3.5 ml) was added and the mixture was refluxed for one hour. A solution of 2-adamantanone 5 (822 mg, 5.47 mmol) and of the methyl benzoate ester 4b prepared previously (1.2 g, 444.50 mmol) in anhydrous THF (10 ml) was added dropwise to the mixture. The reaction mixture was refluxed for 3 hours. Water was added carefully to the mixture at 0° C., which was then diluted with diethyl ether. The organic phase was washed with a saturated solution of NaCl, then dried over MgSO$_4$ and concentrated under reduced pressure. Chromatography on silica gel using cyclohexane/EtOAc (v/v:99/1) as eluent mixture made it possible to obtain 2-[1-(3-tert-butyldimethylsilyloxy) phenyl)-1-methoxy-methylene]tricyclo[3.3.1.1]decane 3b (796 mg, 66%) in the form of a colorless oil. $^1$H NMR (CDCl$_3$, 300 MHz) δ 7.09 (t, 1H), 6.81 (d, 1H), 6.70 (m, 2H), 3.20 (s, 3H), 3.14 (br s, 1H), 2.54 (br s, 1H), 1.87-1.67 (m, 12H), 0.91 (s, 9H), 0.14 (s, 6H). $^{13}$C NMR (CDCl$_3$, 75 MHz) δ 155.5, 143.6, 136.9, 131.2, 129.0, 122.6, 121.2, 119.5, 57.6, 39.3, 39.2, 38.9, 37.4, 32.9, 30.5, 25.8, 18.3, −4.70.

A solution of n-Bu$_4$NF in THF (2.1 ml, 2.1 mmol, 1.0M) was added to a solution of 2-[1-(3-tert-butyldimethylsilyloxy)phenyl)-1-methoxymethylene]tricyclo-[3.3.1.1$^{3,7}$]decane 3b (740 mg, 1.91 mmol) in dry THF (12 ml). The reaction mixture was stirred for 15 minutes at ambient temperature. The mixture was diluted in diethyl ether (30 ml) and washed with a saturated solution of NaCl. The organic phase was dried over MgSO$_4$ and concentrated under reduced pressure to give, as crude product, 2-[1-(3-hydroxy)phenyl)-1-methoxymethylene]tricyclo[3.3.1.1$^{3,7}$]decane 3a in the form of a yellow oil. $^1$H NMR (CDCl$_3$, 300 MHz) δ 7.19-6.67 (m, 4H), 3.67 (s, 3H), 3.30 (br s, 1H), 3.1 (br s, 1H), 2.50 (br s, 2H), 1.87-1.64 (m, 10H).

Example 3

Dioxetane

Synthesis of the Chemiluminescent Derivative According to the Invention (1)

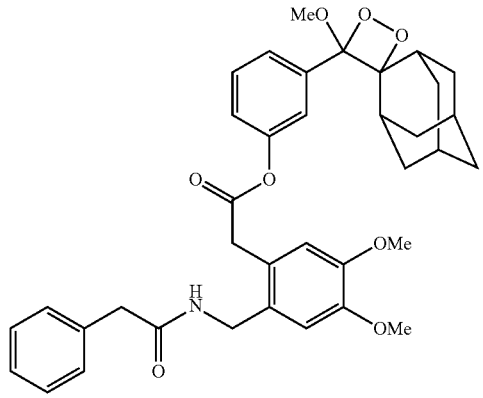

(1)

2-[1-(3-Hydroxy)phenyl)-1-methoxymethylene]tricyclo [3.3.1.1$^{3,7}$]decane 3a (520 mg), triethylamine (800 µl) and benzotriazol-1-yloxytris(dimethylamino)-phosphonium hexafluorophosphate (BOP) (950 mg) were added to a solution of 4,5-dimethoxy-2-[(phenylacetamino)methyl]phenylacetic acid 7 (656 mg, 1.91 mmol) in anhydrous DMF (10 ml). The reaction mixture was stirred at ambient temperature for 6 hours. The mixture was concentrated under vacuum. Chromatography on silica gel using cyclohexane/EtOAc (v/v:40/60) as eluent gave the ether of 3-(adamantan-2-ylidene-methoxymethyl)phenyl enol ester of [4,5-dimethoxy-2-(phenylacetylaminomethyl)phenyl]-acetic acid 2 (606 mg, 53%) in the form of a white powder. M.p. 95° C. $^1$H NMR (CDCl$_3$, 300 MHz) δ 7.21 (t, J=7.9 Hz, 1H), 7.15-7.00 (m, 6H), 6.91 (t, J=2.3 Hz, 1H), 6.84 (ddd, J=7.9 Hz, 2.3 Hz, 0.8 Hz, 1H), 6.80 (s, 1H), 6.77 (s, 1H), 4.44 (d, J=5.3 Hz, 2H), 3.88 (s, 3H), 3.85 (s, 2H), 3.81 (s, 3H), 3.53 (s, 2H), 3.30 (s, 3H), 3.25 (br s, 1H), 2.66 (br s, 1H), 1.90-1.55 (m, 12H). $^{13}$C NMR (CDCl$_3$, 75 MHz) δ 150.6, 148.6, 148.5, 142.6, 137.3, 134.9, 132.9, 129.4, 129.1, 128.9, 127.3, 127.1, 124.1, 122.1, 120.4, 113.5, 112.9, 58.0, 56.1, 56.0, 43.9, 41.4, 39.3, 39.1, 38.3, 37.2, 32.2, 30.3, 28.3. M.S. (Maldi-T of, positive mode) m/z 634.27 [M+K]$^+$, 618.30 [M+Na]$^+$. Analysis calculated for C$_{37}$H$_{41}$NO$_6$: C=74.60, H=6.94 and N=2.35. Analysis measured: C=74.25, H=7.09 and N=2.41.

Ozone was sparged through a cooled solution (−78° C.) of freshly distilled triphenyl phosphite (37 µl, 0.14 mmol) in 9 ml of anhydrous CH$_2$Cl$_2$ until the appearance of a slight blue coloration. The reaction medium was then purged with argon until the blue coloration disappeared. The ether of enol 2 previously synthesized (21 mg, 0.035 mmol) dissolved in 1 ml of anhydrous CH$_2$Cl$_2$ was added at −78° C. The reaction mixture obtained was stirred at −30° C. for 1.5 hours and left to heat up to ambient temperature for 2 hours. After a control HPLC (system A), the reaction mixture was evaporated to dryness. The oily residue obtained was purified by semi-preparative HPLC (system B). The fractions containing the product (retention time T$_R$=48-50 min) were partially evaporated then freeze-dried to give the dioxetane 1 in the form of a white powder (around 1 mg, yield 5%). HPLC (system C), T$_R$ 23.8 min. UV (recorded during the HPLC analysis) λ$_{max}$ 235 and 281 nm. MS (ESI, positive mode) m/z 650.0 (M+Na)+(molecular weight calculated: 627.74 for C$_{37}$H$_{41}$NO$_8$).

The invention claimed is:
1. A compound of general formula (I):

S—B-A in which:
S represents a labile structure that can be activated by a biological entity, and S having the general formula (VI):

P-L-☐ in which:
☐ symbolizes a covalent bond with B;
P represents a substrate that can be recognized by the biological entity; and
L represents an oxygen, sulfur, nitrogen, carbonyl or a —CO-Q- functional group, with Q being O, S or NH;
B is a reactive branch, of which the chemical structure is such that the activation of the labile structure S induces intramolecular rearrangement in a suitable form for releasing a molecule A$^−$; and B having the general formula (III):

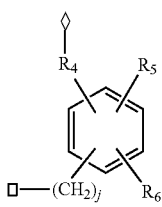

in which:
□ and ◇ symbolize, respectively, a covalent bond with the labile structure S and a chromophore A;
j is an integer ranging from 0 to 2;
$R_4$ is a $C_1$-$C_{20}$ hydrocarbon-based chain, where appropriate interrupted by one or more heteroatoms and/or space —CO and/or —N(alkyl)-unit(s), located ortho, meta or para to the □-$(CH_2)_j$-radical, and chosen from —$(CH_2)_k$-◇, —$(CH_2)_k$—C(O)-◇, and —$CH_2$—O—C(O)—N($CH_3$)—$(CH_2)_2$—N($CH_3$)—C(O)-◇ radicals, with k being equal to 1 or 2;
$R_5$ and $R_6$ are, independently of one another, a hydrogen atom or a saturated or unsaturated, linear, branched or cyclic, $C_1$-$C_{20}$ hydrocarbon-based chain chosen from an alkyl radical, an alkoxy radical, an alkylamino or dialkylamino radical, an alkylthio and a $C_6$-$C_{30}$ aromatic ring chosen from an aryl radical, an aryloxy radical, an arylamino radical and an arylthio radical
A is a chromophore of formula (IIa):

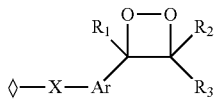

in which:
◇ symbolizes the covalent bond with B;
$R_1$ is a saturated or unsaturated, linear, branched or cyclic, $C_1$-$C_6$ alkyl or $C_1$-$C_6$ alkoxy radical, optionally comprising one or more atoms chosen from O, N and S, and is optionally substituted;
$R_2$ and $R_3$ are linked to form a spiro adamantyl radical with the carbon of the dioxetane ring which bears $R_2$ and $R_3$ substituted where appropriate;
Ar represents a $C_6$-$C_{30}$ arylene radical of general formula (IVa):

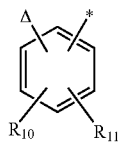

in which:
Δ symbolizes a covalent bond with X and * symbolizes a covalent bond with the dioxetane ring;
$R_{10}$ represents a hydrogen atom, an electroactive radical or a fluorescent radical; and
$R_{11}$ is chosen from a hydrogen atom and a $C_6$-$C_{10}$ aryl radical fused with the phenylene radical, and
X represents O, NH or S;
and derivatives thereof.

2. The compound as claimed in claim 1, wherein $R_1$ is a fluorescent radical.

3. The compound as claimed in claim 1, wherein $R_1$ is a fluorescent radical, it is chosen from phenyl and its derivatives, naphthalene and its derivatives, anthracene and its derivatives, pyrene and its derivatives, biphenyl and its derivatives, acridine and its derivatives, coumarin and its derivatives, xanthene and its derivatives, phthalocyanine and its derivatives, stilbene and its derivatives, furan and its derivatives, oxazole and its derivatives, oxadiazole and its derivatives, nitrobenzoxadiazole and its derivatives, benzothiazole and its derivatives, fluorescein and its derivatives, rhodamine and its derivatives, BODIPY and its derivatives, eosin and its derivatives, erythrosine and its derivatives, resorufin and its derivatives, quinoline and its derivatives, carbazole and its derivatives, fluorescent cyanines and derivatives, carbocyanine and its derivatives, pyridinium salts and derivatives, a fluorescent complex of lanthanides and its derivatives, fluorescent proteins and quantum dots.

4. The compound as claimed in claim 1, wherein $R_1$ and/or $R_{10}$ is a fluorescent radical chosen from phenyl and its derivatives, naphthalene and its derivatives, anthracene and its derivatives, pyrene and its derivatives, biphenyl and its derivatives, acridine and its derivatives, coumarin and its derivatives, xanthene and its derivatives, phthalocyanine and its derivatives, stilbene and its derivatives, furan and its derivatives, oxazole and its derivatives, oxadiazole and its derivatives, nitrobenzoxadiazole and its derivatives, benzothiazole and its derivatives, fluorescein and its derivatives, rhodamine and its derivatives, BODIPY and its derivatives, eosin and its derivatives, erythrosine and its derivatives, resorufin and its derivatives, quinoline and its derivatives, carbazole and its derivatives, fluorescent cyanines and derivatives, carbocyanine and its derivatives, pyridinium salts and derivatives, a fluorescent complex of lanthanides and its derivatives, fluorescent proteins and quantum dots.

5. The compound as claimed in claim 1, wherein $R_{10}$ is an electroactive radical chosen from a halogen atom, a cyano radical, a nitro radical, a monosubstituted or disubstituted amide radical, an alkyl radical, an alkoxy radical, a trialkylammonium radical, an alkylamido radical, an alkylcarbamoyl radical, an ester radical, an alkylsulfonamido radical, a trifluoromethyl radical, an alkylsilyl, dialkylsilyl or trialkylsilyl radical, an alkylsiloxy, dialkylsiloxy or trialkylsiloxy radical, an alkylamidosulfonyl radical, an alkylsulfonyl radical, an alkyl thioether radical, a haloalkyl radical, a $C_6$-$C_{10}$ radical chosen from an aryloxy radical, an arylamido radical, an arylcarbamoyl radical, an arylsulfonamido radical, an aryl radical, a heteroaryl radical, a triaryl or alkylarylsilyl radical, a triarylsiloxy radical, an arylamidosulfonyl radical, an arylsulfonyl radical and an aryl thioether radical.

6. The compound as claimed in claim 1, wherein X represents O.

7. The compound as claimed in claim 1, wherein the compound has the formula (Va):

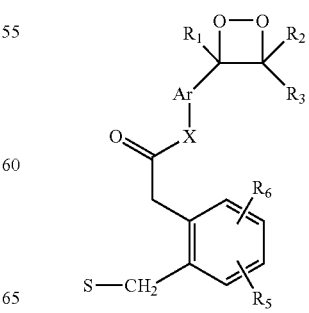

8. The compound as claimed in claim 1, wherein the compound has the formula (Vb):

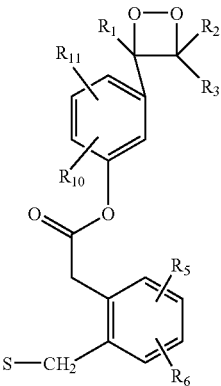

9. The compound as claimed in claim 8, wherein $R_{10}=R_{11}=H$, $R_1=R_5=R_6=$—O—$CH_3$, and $R_2$ and $R_3$ are linked to form a spiro adamantyl radical with the carbon of the dioxetane ring which bears $R_2$ and $R_3$, substituted where appropriate.

10. The compound as claimed in claim 1, wherein S represents a structure that is labile by action of an enzyme.

11. The compound as claimed in claim 10, wherein S represents a structure that is labile by action of a protease, L represents —CO-Q, with Q being NH, and P represents a substrate recognized by the protease.

12. The compound as claimed in claim 1, wherein it is a derivative of formula (VII):

D-S—B-A in which:

D represents a target structure.

13. The compound as claimed in claim 12, wherein the target structure D is chosen from a lectin, an antibody or a fragment of the antibody; a cell receptor ligand; a ligand capable of interacting with a membrane lipid or phospholipid; and a ligand capable of interacting with a sugar present at the surface of cells.

14. A pharmaceutical composition comprising at least an effective amount of at least one compound as defined in claim 1.

15. A method for detecting and/or quantifying a biological entity, using at least one compound as claimed in claim 1, in which S represents a labile structure that can be activated by the entity.

16. A method for detecting and/or quantifying a biological entity comprising at least the steps of:
bringing at least an effective amount of at least one compound as defined in claim 1 in which S represents a labile structure that can be activated by said biological entity to be detected and/or quantified, into contact with a medium assumed to comprise said entity; and
measuring the luminescent signal generated.

17. The method as claimed in claim 16, wherein the compound is:

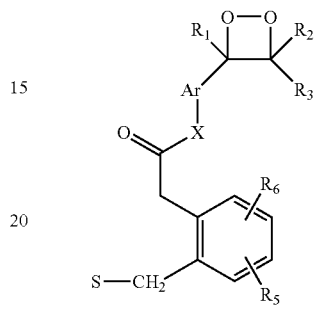

18. The method as claimed in claim 16, carried out in vitro comprising the step of adding a light amplifier chosen from fluorescein, bovine albumin, human albumin, polymeric quaternary onium salts, a sodium salt of fluorescein, and poly (benzyltributyl)ammonium.

19. The method as claimed in claim 16, wherein the biological entity to be detected and/or quantified is an enzyme and wherein S in the compound of general formula (I) represents a substrate that can be activated by the enzyme.

20. A kit for the detection and/or quantification via detection of a biological entity comprising at least one compound as defined in claim 1, in which S represents a labile structure that can be activated by said biological entity to be detected and/or quantified.

21. The diagnostic method in vivo using a pharmaceutical composition comprising a compound as defined in claim 1.

22. The compound as claimed in claim 1, wherein $R_2$ and $R_3$ are substituted by radicals $R_8$ and/or $R_9$, wherein $R_8$ and $R_9$ are, independently of one another, an electroactive radical chosen from a hydroxyl radical, a halogen atom, a cyano radical, an amide radical, an alkoxy radical, a haloalkyl radical, a phenyl radical and an alkoxyphenyl radical.

23. The method as claimed in claim 18, wherein the polymeric quaternary onium salts are chosen from poly(vinylbenzyltrimethyl)ammonium chloride (TMQ), poly(vinylbenzyltributyl)ammonium chloride (TBQ), poly(vinylbenzyldimethyl)ammonium chloride (BDMQ), poly(vinylbenzyltributyl)phosphonium chloride, poly(vinylbenzyltributyl)sulfonium chloride, and poly(benzyldimethylvinylbenzyl)ammonium chloride.

* * * * *